United States Patent [19] [11] 4,379,462
Borkan et al. [45] Apr. 12, 1983

[54] MULTI-ELECTRODE CATHETER ASSEMBLY FOR SPINAL CORD STIMULATION

[75] Inventors: William N. Borkan, North Miami; Frank M. Savino, Fort Lauderdale, both of Fla.; Joseph M. Waltz, Rye, N.Y.

[73] Assignee: Neuromed, Inc., Fort Lauderdale, Fla.

[21] Appl. No.: 201,783

[22] Filed: Oct. 29, 1980

[51] Int. Cl.³ .............................................. A61N 1/04
[52] U.S. Cl. .................................................... 128/786
[58] Field of Search .............................. 128/784–786, 128/419 P, 419 C, 642

[56] References Cited

U.S. PATENT DOCUMENTS

| | | | |
|---|---|---|---|
| 3,348,548 | 10/1967 | Chardack | 128/786 |
| 3,367,339 | 2/1968 | Sessione | 128/786 |
| 3,769,984 | 11/1973 | Muench | 128/786 |
| 3,825,015 | 7/1974 | Berkovits | 128/786 |
| 3,890,977 | 6/1975 | Wilson | 128/785 X |
| 3,995,623 | 12/1976 | Blake et al. | 128/786 |
| 4,044,774 | 8/1977 | Corbin et al. | 128/784 |
| 4,141,365 | 2/1979 | Fischell et al. | 128/642 |
| 4,285,347 | 8/1981 | Hess | 128/786 |

FOREIGN PATENT DOCUMENTS 7157  1/1980  European Pat. Off. ............ 128/784

OTHER PUBLICATIONS

"USCI Catalog", Jun. 1974, pp. 1–12.

Primary Examiner—Lee S. Cohen
Attorney, Agent, or Firm—Leitner, Palan, Martin & Bernstein

[57] ABSTRACT

A catheter electrode assembly having four equally spaced in-line electrodes along the exterior of the sheath at the distal end and are interconnected to terminals at the proximal end by sets of individually insulated stranded stainless steel wire. The catheter electrode assembly is used for spinal cord stimulation and may be connected by a percutaneous extension to the exterior of the body for testing and evaluation. A permanent full length or partial length stiffening wire or a removable stylet may be provided interior the sheath.

16 Claims, 5 Drawing Figures

MULTI-ELECTRODE CATHETER ASSEMBLY FOR SPINAL CORD STIMULATION

BACKGROUND OF THE INVENTION

The present invention relates generally to catheter electrodes and more specifically to a catheter electrode for use in stimulating the spinal cord.

In recent years the application of the spinal cord stimulation has shown a great deal of promise in the treatment of pain and various motor disorders. Initially the leads were implanted in the cervical area by a small laminectomy and applied to the dura in the epidural space along the midline under direct vision. This requires an operation in the cervical area where two or three spinous processes and one set of lamina are removed.

The next generation of stimulation electrodes were positioned by percutaneous implantation. This procedure could be carried out under a local anesthetic. The electrodes were passed into the epidural space while being monitored by flouroscopy until they were placed at the desired level. Unfortunately, the only electrodes that were presently available were single electrodes. Thus, it was necessary to make two separate puncture wounds and position two independent electrodes along the midline of the spinal cord. A description of the prior art devices and the improvement thereto is described in U.S. Pat. No. 4,044,774.

Due to the particularities in the construction of the electrodes illustrated in the aforementioned patent, it was not possible to produce a multi-electrode catheter. The main reason for this difficulty was that the conductors connecting the contacts to the leads used a wire coiled in a helix construction. To manufacture a multi-electrode assembly would have necessitated a special insulation and manufacturing process to accommodate additional coiled conductors in the same sheath and would possibly unduly increase the diameter of the sheath.

Other problems with prior art percutaneous implanted electrodes included broken wires, displaced electrodes and the general inability to achieve satisfactory, consistent, in-line placement. The placement factor became more critical in view of recent studies that polarity plays a major role in the effectiveness of the stimulation. Thus the trend has been back to placing the electrodes in position via a laminectomy.

Multiple electrode catheters have been used in the prior art and have been directed specifically to the stimulation of the heart muscle. Typical patents are U.S. Pat. Nos. 3,348,548; 3,825,015; and 3,995,623. The spacing of the electrodes and design vary with the portions of the heart to which they desire to stimulate.

The prior art has failed to direct its efforts for providing a multiple electrode catheter which can be percutaneously inserted for spinal cord stimulation.

Catheter electrodes now being manufactured for cardiac pacing are not suitable for spinal cord stimulation since their strength is questionable under stresses imposed by placement in the spinal column. The diameter of most cardiac leads are also larger than those desirable for use in the spinal column.

SUMMARY OF THE INVENTION

An object of the present invention is to provide a multi-electrode catheter for use in spinal cord stimulation.

Another object of the present invention is to provide a plural electrode catheter which may be percutaneously positioned with a minimum amount of surgery, time and patient trauma.

A further object of the present invention is to provide a plural electrode catheter with conductors having an extended life for long-term stimulation.

A still further object of the present invention is to provide a catheter electrode which is capable of the same accuracy of positioning as an electrode system implanted by a laminectomy.

These and other objects of the invention are attained by a catheter electrode assembly having at least three electrodes equally spaced along the distal end of the assembly. At least three in-line terminals at the proximal end of the assembly are connected to a respective distal electrode by a set of stranded stainless steel wires. The electrodes that are bonded to the surface of the sheath of the catheter assembly, have a length of 4 millimeters and are spaced 6 millimeters apart. A permanent stiffening wire may be provided for either the total length or just for the length of the tip portion of the catheter electrode assembly to improve steerability and aid placement. Alternatively a removable stylet may be provided. A percutaneous extension mated to the terminals at the proximal end allows percutaneous stimulation for testing the placement and effectiveness.

DESCRIPTION OF THE PREFERRED EMBODIMENTS

Figure 1:
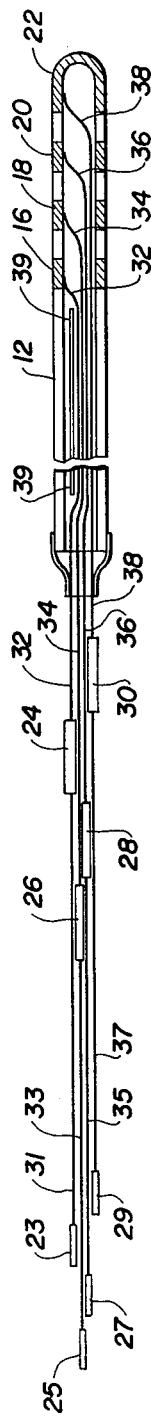
FIG. 1 is a cross-sectional view of a catheter electrode assembly incorporating the principles of the present invention.

A catheter electrode 10 as illustrated in FIG. 1 includes a sheath 12. A plurality of equally spaced electrodes 16, 18, 20 and 22 attached to the distal end and a plurality of terminals 24, 26, 28 and 30 are located at the proximal end of the catheter electrode assembly 10. A set of individually insulated stranded stainless steel wires 32, 34, 36 and 38 interconnects the electrodes 16, 18, 20 and 22 with the terminals 24, 26, 28 and 30, respectively. These wires 32, 34, 36 and 38 are substantially parallel in the catheter sheath 12.

In this embodiment a stiffening wire 39 which cannot be removed is shown inside the sheath adjacent to the stainless steel wires. This wire is typically insulated and improves the steerability of the assembly. The stiffening wire 39 may run the entire length of the electrode assembly or just a portion thereof extending from the distal end approximately 15 centimeters. The shorter stiffening wire allows flexibility of the catheter assembly at the exit point from the spinal column. The stiffening wire may be an extrude non-metallic material or a single wire or a plurality of stranded wires insulated as a group.

The external terminals 23, 25, 27 and 29 are connected to the terminals 24, 26, 28 and 30 by wires 31, 33, 35 and 37, respectively, and are used for percutaneous testing during a trial period of stimulation. The wires 31, 33, 35 and 37 are cut and removed prior to permanent implantation.

Figure 2:
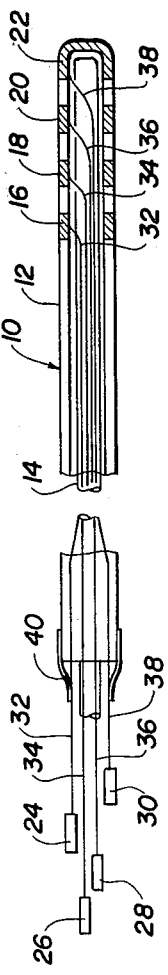
FIG. 2 is a cross-sectional view of another embodiment of a catheter electrode assembly incorporating the principles of the present invention including a removable stylet.

The catheter electrode 10 of FIG. 2 also includes a sheath 12 with an internal tube 14. A plurality of equally spaced electrodes 16, 18, 20 and 22 are attached at the distal end of the catheter electrode assembly 10 and a plurality of terminals 24, 26, 28 and 30 are located at the proximal end of the catheter electrode assembly 10. A set of individually insulated stranded stainless steel wires 32, 34, 36 and 38, interconnect the electrodes 16, 18, 20 and 22 and the terminals 24, 26, 28 and 30, respectively. Each set of stranded stainless steel wire includes, for example, 90 strands of 12 micron wire. The wire is specially coated with Teflon for insulation and hermetic sealing to withstand the environment of the human body. To decrease the breakage of the interconnection of the stainless steel wires to the electrode and terminals, they may be joined by welding or specialized soldering technique.

The sets of stranded stainless steel wire 32, 34, 36 and 38 run substantially parallel inside the sheath 12. The tube 14 accommodates a metal stylet which is inserted therein to aid insertion of the catheter electrode assembly and is removed after placement. A sleeve 40 extends across the proximal end of the electrode assembly 10 and is sealed to the internal tube 14 with an epoxy adhesive. This holds the set of wires 32, 34, 36 and 38 in place.

In the embodiment illustrated in FIG. 1, the wires 32, 34, 36 and 38 extend beyond the end of the sheath 14 with the terminals 24, 26, 28 and 30 being arranged in a staggered in-line configuration. This staggered in-line configuration increases the compactness of the overall electrode assembly and allows it to be readily inserted through a relatively small needle.

An example of typical materials and dimensions for the catheter electrode assembly 10 includes an outside diameter of approximately 0.047 inches. The electrodes 16, 18, 20 and 22 are preferably platinum electrodes having a length of 4 millimeters and a spacing of 6 millimeters. The sheath 12 is preferably a radiopaque medical grade polyethylene material. The electrodes are secured to the sheath by epoxy adhesive bonding. The terminals 24, 26, 28 and 30 may be stainless steel tubes. The catheter electrode assembly having these dimensions may be inserted through a thin wall sixteen gauge needle. The overall length of the catheter electrode assembly would be in the range of 40 cm to 60 cm.

Figure 3:
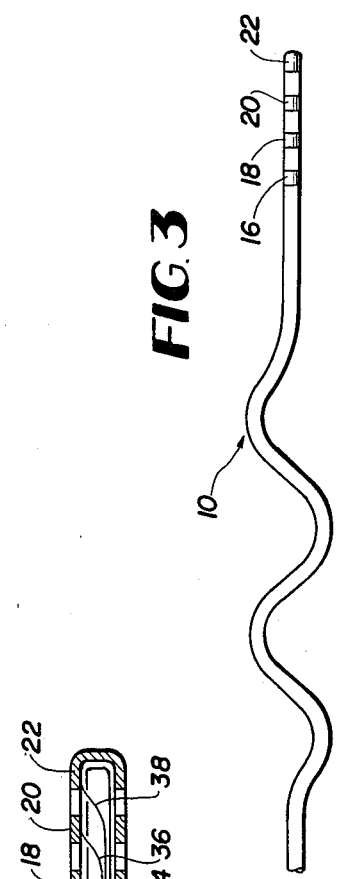
FIG. 3 is a plan view of the catheter electrode of FIG. 2 after removal of the stylet.

The catheter electrode assembly 10 may be inserted into the epidural space and positioned with the assistance of a removable stylet inserted through internal tube 14. Once proper positioning has been accomplished, adjacent to the spinal cord, the stylet is removed and a preformed S-bend in the catheter electrode assembly returns to its S-shape as illustrated in FIG. 3. This S-shape curve helps to stablilize the electrode position for long periods of time.

The particular configuration of the terminals 24, 26, 28 and 30 of FIG. 1 is to allow their connection to presently available receivers which are implanted within the body. After testing, the appropriate set of leads may be selected to be connected to the internal stimulator. This is generally a receiver which receives external signals to produce the appropriate stimulation. Substantial work has been performed which indicates that the appropriate leads and their polarity vary depending upon the disorder to be corrected and the individual upon which the stimulation is being performed.

Figure 4:
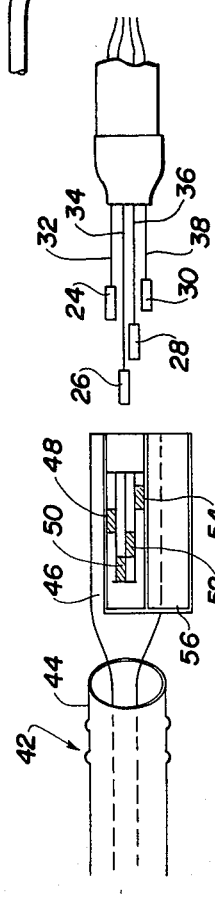
FIG. 4 is a plan view of a percutaneous extension incorporating the principles of the present invention.

To facilitate the external testing of the patient to find the appropriate set of leads and polarity, a separate percutaneous extension is provided for the embodiment shown in FIG. 2. As illustrated in FIG. 4, the percutaneous extension 42 includes a cord set 46 and a boot 44. In an opening in the face of the cord set 46 are a plurality of conductive connectors 48, 50, 52 and 54. These connectors receive the terminals 24, 26, 28 and 30, respectively, of the catheter electrode assembly 10. Once the terminals of the catheter electrode are mated with the connectors of the percutaneous extension, a cap 56 is rotated over and covers the opening in the cord set 46. The boot 44 is slid over the entire assembly. A medical grade silicone adhesive may be applied to effectively seal the connections for biocompatibility. The cord set 46 extending from the boot 44 is designed to fit through an extremely small needle so as to minimize the chance of infection during the period of percutaneous testing. The material for the cord set is preferably silastic. Other types of extensions may be used.

Figure 5:
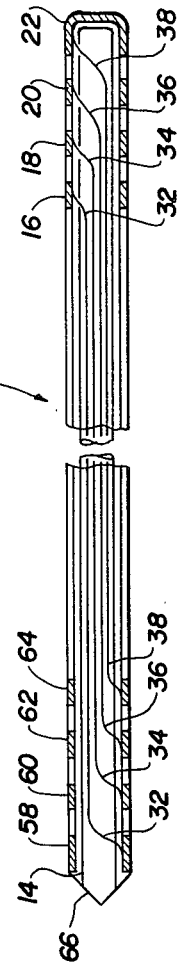
FIG. 5 is a cross-sectional view of even a further embodiment of a catheter electrode incorporating the principles of the present invention.

Another embodiment of catheter electrode of the present invention is illustrated in FIG. 5. The catheter electrode includes the same configuration at the distal end having four equally spaced electrodes along the exterior of the sheath. At the proximal end, major modification includes for equally spaced terminals 58, 60, 62 and 64 mounted to the exterior of the sheath 12 in the same manner as the electrodes at the distal end. This set of stainless steel wires 32, 34, 36 and 38 interconnect the electrodes 16, 18, 20 and 22 and the terminals 58, 60, 62 and 64. This embodiment includes a stiffening wire which is a permanent part of the electrode assembly and which may run all or a portion of the length of the electrode assembly. End terminal 58 is a cap terminal similar to electrode 22. This provides a completely sealed, highly reliable electrode system. A modified separate percutaneous extension of the type described above may also be used for a trial period of stimulation.

The technique to use and implant the present catheter electrode system involves the initial implantation of the catheter electrode under general anesthesia through a percutaneous needle. The electrode system has temporary extensions which are brought out through the skin to allow the testing at various levels of stimulation on the patient. With the four electrode system there are eighteen possible combinations. An electrode analysis is performed which requires approximately two weeks with changes being made daily. It has been found the patients respond to specific electrode combinations, polarity and positioning and this electrode analysis is an extremely crucial part of the technique. Following the determination of the most ideal electrode combination, the system is permanently internalized and attached to a subcutaneously placed receiver. During the postoperative period, which lasts for approximately 7-10 days, frequency analysis is carried out and the patient is tested in frequencies ranging from 10 to 1400 hertz. It has been found that great variability occurs in the patient in response to frequency, with many of the patients responding much better in the high frequency range rather than the low. Hospitalization requires approximately four weeks wherein future follow-up of the patient is carried out. Treatment of patients with motor disorders including cerebral palsy, dystonia, torticollis, poststroke and posttraumatic syndrome.

A distinct area of response was observed in these patients between the 2nd and 4th cervical vertebrae (C2-C4) and was found to be highly responsive to stimulation. Best results were obtained when the electrodes were placed in this region. Thus there was a need for an electrode which would stimulate the area between C2 and C4 vertebrae for best results. For this reason, the present catheter electrode system is designed with four in-line electrodes which will allow the flexibility of selecting the appropriate area between the C-2 and C-4 vertebrae for stimulation. It is important that this electrode assembly be a catheter style electrode for ease of placement as described above. The use of the catheter electrode eliminates the need for a major operation and is more comfortable for the patient. Neither the percutaneous needle used for insertion nor the electrode system comes in contact with the spinal cord and remains outside the dura.

From the preceding description of the preferred embodiments it is obvious that the objects of the invention are attained in that an improved catheter electrode assembly having a plurality of in-line electrodes is provided which allows more accurate stimulation of the spinal cord with a minimum of incisions. Similarly, the specific materials, their dimensions and interconnections increase the reliability and life of the electrode. Although the invention has been described and illustrated in detail, it is clearly understood that the same is by way of illustration and example only and is not to be taken by way of limitation. The spirit and scope of the invention are to be limited only by the terms of the appended claims.

What is claimed:

1. A catheter electrode assembly for insertion through a needle to lie along and stimulate the spinal cord comprising:
   a sheath having a distal and a proximal end and an outer diameter of less than approximately 0.05 inches;
   at least three in-line electrodes equally spaced along the exterior of said distal end of said sheath to lie in-line along a spinal cord;
   at least three in-line terminals at the proximal end of said sheath; and
   at least three sets of individually insulated stranded stainless steel wires interconnecting an electrode and a respective terminal, the insulation of said sets of wires hermetically seals said sets of wires independent of said sheath without reducing the flexibility of said sets of wires.

2. The catheter electrode assembly according to claim 1 wherein said wires are attached to said electrodes and terminals by a weld or solder.

3. The catheter electrode assembly according to claim 1 wherein said electrodes have a length of four millimeters and are spaced six millimeters apart.

4. The catheter electrode assembly according to claim 1 including a tube interior to and coaxial with said sheath for insertion of a stylet within said tube; and wherein said sets of wires are between said sheath and said tube.

5. The catheter electrode assembly according to claim 4 wherein said electrodes are bonded to the exterior of said sheath.

6. The catheter electrode assembly according to claim 1 wherein each set of wire includes ninety strands of twelve micron wire.

7. The catheter electrode assembly according to claim 1 wherein each set of wire is coated with Teflon.

8. The catheter electrode assembly according to claim 1 wherein said electrodes and said terminals are bonded to said sheath.

9. The catheter electrode assembly according to claim 1 wherein said terminals and a portion of said wires extend from the proximal end of said sheath to permit attachment to an external signal source.

10. The catheter electrode assembly according to claim 9 wherein the proximal end of the sheath is sealed.

11. A catheter electrode assembly for spinal cord stimulation comprising:
    a sheath having a distal and a proximal end and an outer diameter of less than approximately 0.05 inches;
    a plurality of spaced in-line electrodes along the exterior of the distal end of said sheath to lie in-line along a spinal cord;
    a plurality of in-line terminals at the proximal end of said sheath;
    a plurality of sets of individually insulated stranded wires in said sheath each interconnecting an electrode and a respective terminal, the insulation of said sets of wires hermetically seals said sets of wires independent of said sheath without reducing the flexibility of said sets of wires; and
    a stiffening wire in said sheath for improving the steerability of the catheter assembly.

12. The catheter assembly according to claim 11 wherein said stiffening wire extends the entire length of said sheath.

13. The catheter assembly according to claim 11 wherein said stiffening wire extends from the distal end of said sheath and terminates short of the proximal end to allow flexibility of the catheter assembly at the exit point of the spinal cord.

14. The catheter assembly according to claim 11 wherein said stiffening wire is an extruded non-metallic material.

15. The catheter assembly according to claim 11 wherein said stiffening wire is an insulated stranded stainless steel wire.

16. A method of treating neurological motor disorders comprising:
    inserting a catheter electrode assembly through a percutaneous needle into the space external the dura and positioned adjacent the spinal column in the area between the second and fourth cervical vertebrae;
    said catheter electrode assembly including a sheath with a plurality of spaced in-line electrodes along the exterior of the distal end of said sheath and a plurality of in-line terminals at the proximal end of said sheath, and a plurality of sets of individually insulated and hermetically sealed stranded wires in said sheath each interconnecting an electrode and a respective terminal;
    applying electrical signals to pairs of said terminals to determine the most effective combination;
    removing said percutaneous needle; and
    implanting a receiver and connecting said terminals to said receiver to provide stimulation pulses to a selected pair of electrodes.

* * * * *